United States Patent
Grass et al.

(10) Patent No.: US 9,987,503 B2
(45) Date of Patent: *Jun. 5, 2018

(54) FLEXIBLE X-RAY, DETECTOR WITH OPTICAL SHAPE SENSING

(71) Applicant: KONINKLIJKE PHILIPS N.V., Eindhoven (NL)

(72) Inventors: Michael Grass, Buchholz in der Nordheide (DE); Robert Manzke, Bonebuttel (DE); Raymond Chan, San Diego, CA (US)

(73) Assignee: Koninklijke Philips N.V., Eindhoven (NL)

(*) Notice: Subject to any disclaimer, the term of this patent is extended or adjusted under 35 U.S.C. 154(b) by 818 days.

This patent is subject to a terminal disclaimer.

(21) Appl. No.: 14/356,188

(22) PCT Filed: Oct. 29, 2012

(86) PCT No.: PCT/IB2012/055968
§ 371 (c)(1),
(2) Date: May 5, 2014

(87) PCT Pub. No.: WO2013/068877
PCT Pub. Date: May 16, 2013

(65) Prior Publication Data
US 2014/0357988 A1    Dec. 4, 2014

Related U.S. Application Data

(60) Provisional application No. 61/556,315, filed on Nov. 7, 2011.

(51) Int. Cl.
*A61N 5/10*      (2006.01)
*G01T 1/161*    (2006.01)
(Continued)

(52) U.S. Cl.
CPC .............. *A61N 5/1067* (2013.01); *A61B 6/12* (2013.01); *A61N 5/1071* (2013.01); *G01T 1/023* (2013.01); *G01T 1/161* (2013.01)

(58) Field of Classification Search
CPC ........... G01T 1/161; G01T 1/023; A61B 6/12; A61N 5/1071; A61N 5/1067
See application file for complete search history.

(56) References Cited

U.S. PATENT DOCUMENTS

| | | | |
|---|---|---|---|
| 5,088,492 A | | 2/1992 | Takayama et al. |
| 5,793,046 A | * | 8/1998 | Jeffers ...................... G01T 1/20 250/364 |

(Continued)

FOREIGN PATENT DOCUMENTS

| | | |
|---|---|---|
| CN | 101416878 A | 4/2009 |
| JP | 2006158678 | 12/2004 |

(Continued)

OTHER PUBLICATIONS

Logier et al., OFSETH: Smart medical textile for continuous monitoring of respiratory motions under magnetic resonance imaging, 31st Annual International Conference of the IEEE EMBS, Minneapolis, Minnesota, USA, Sep. 2-6, 2009.*

*Primary Examiner* — Bo J Peng (57) ABSTRACT

The present invention relates to a sensor device for detecting dose of radiation received at the sensor device, the sensor device comprising a flexible body having a cross-section being comparatively small relative to the length of the device, a cladding at the flexible body, the cladding converting incoming radiation into visible light, and an optical shape sensing device disposed within the flexible body and configured to determine a shape of the flexible instrument relative to a reference, the shape sensing device configured to collect information based on its configuration to map an intraluminal structure during a procedure. The present invention further relates to a radiation therapy system including such a sensor device and a method of operating a radiation therapy system including such a sensor device.

13 Claims, 4 Drawing Sheets

(51) Int. Cl.
*A61B 6/12* (2006.01)
*G01T 1/02* (2006.01)

(56)  References Cited

U.S. PATENT DOCUMENTS

| | | |
|---|---|---|
| 6,612,992 B1 | 9/2003 | Hossack et al. |
| 7,180,069 B2 | 2/2007 | Motomura et al. |
| 7,791,046 B2 | 9/2010 | Laine et al. |
| 7,831,016 B2 | 11/2010 | Saoudi et al. |
| 8,864,655 B2 | 10/2014 | Ramamurthy et al. |
| 2002/0183592 A1 | 12/2002 | Suzuki et al. |
| 2004/0165810 A1 | 8/2004 | Fujita |
| 2005/0012043 A1 | 1/2005 | Motomura et al. |
| 2005/0075704 A1* | 4/2005 | Tu .................. A61B 18/245 607/88 |
| 2005/0187422 A1 | 8/2005 | Maschke |
| 2009/0123111 A1 | 5/2009 | Udd |
| 2010/0288934 A1 | 11/2010 | Keppel et al. |
| 2013/0131499 A1 | 5/2013 | Chan et al. |

FOREIGN PATENT DOCUMENTS

| | | |
|---|---|---|
| WO | WO200077491 | 12/2000 |
| WO | WO2007131561 | 11/2007 |

\* cited by examiner

FLEXIBLE X-RAY, DETECTOR WITH OPTICAL SHAPE SENSING

CROSS-REFERENCE TO PRIOR APPLICATIONS

This application is the U.S. National Phase application under 35 U.S.C. § 371 of International Application Serial No. PCT/IB2012/055968, filed on Oct. 29, 2012, which claims the benefit of U.S. Application Ser. No. 61/556,315, filed on Nov. 7, 2011. These applications are hereby incorporated by reference herein.

FIELD OF THE INVENTION

The present invention relates to a flexible x-ray detector with optical shape sensing. This present invention relates to medical imaging, and more particularly to systems and methods for mapping internal volumes using a combination of shape sensing and images during medical procedures.

BACKGROUND OF THE INVENTION

In medical procedures a minimally invasive device that can be localized with a high spatial accuracy in real time in 3D and that is able to measure the number of photons reaching the tip of the device may be valuable. E.g., in 4D radiation therapy such a device may be located in the close vicinity of a tumor or even be inserted into the tumor. During radiation therapy the device may then measure the applied dose which is hitting the tumor accurately inside the body of the patient. At the same time the device may provide the 4D position of the tumor during radiation therapy. Thus, high precision radiation therapy can be applied to the tumor. There may well be other medical or non-medical procedures which may profit from such a device. In the following, a very efficient and compact device is introduced and discussed.

As stated above, the present invention generally concerns tracking of elongated devices, particularly optical tracking of medical devices (e.g., endoscopes, catheters and guidewires). The flexible x-ray detector with optical shape sensing may be used for a three-dimensional ("3D") shape reconstruction. The flexible x-ray detector with optical shape sensing utilizes an optical fiber embedded within an elongated device.

The art of shape reconstruction of a multi-core fiber generally involves three steps.

The first step involves a multi-core fiber being interrogated with optical frequency domain reflectometry, which results in the measurement of both an amplitude and a phase of a reflection for each core as a function of wavelength. The reflection may be invoked by embedded periodical structures (e.g., Fiber Bragg Gratings) or by non-periodic, random variations in the refractive index (e.g., Rayleigh scattering).

The second step involves a calculation of strain in each core at multiple positions along the fiber from the reflection spectra.

The third step involves a 3D shape reconstruction of the optical fiber by means of combining the various strain data. In particular, the strain measurements may be converted to rotation angles and the associated rotation matrices may be used to update a tangent vector, a normal vector and a binormal vector (i.e. columns of a Jacobian matrix). However, the art fails to address how the line elements of the fiber are calculated or how the matrix for converting the strain measurements is established.

The inventor of the present invention has appreciated that an improved device for combined detection of position and radiation dose is of benefit, and has in consequence devised the present invention.

SUMMARY OF THE INVENTION

It would be advantageous to achieve a system for radiation therapy where movement in the patient may be compensated for. In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

The present principles can provide benefits such as, e.g., better feedback for a physician on location and progress of radiation therapy within an anatomy of a patient.

To better address one or more of these concerns, in a first aspect of the invention a radiation therapy system is presented that comprises a movable radiation source for directing and providing radiation to a designated target area or target volume, an elongated flexible instrument comprising a sensor device detecting dose of radiation received at the sensor device, the sensor device including a cladding converting incoming radiation into visible light, an optical shape sensing device disposed within the flexible instrument and configured to determine a shape of the flexible instrument relative to a reference, the shape sensing device configured to collect information based on its configuration to map an intraluminal structure during a procedure, a detector connected to the sensor device for detecting the visible light so as to determine the dose of radiation received at the sensor device, and a processor for operating the movable radiation source in relation to a predetermined target radiation dose and the determined dose of radiation.

The radiation therapy system comprises a radiation source, such as an x-ray source or other suitable source for providing radiation for radiation therapy. The radiation source may be mounted on a movable arm thereby providing a movable radiation source for directing and providing radiation to a designated target area or target volume, e.g. direct the radiation to a tumor in a patient.

Further an elongated flexible instrument is provided. The elongated flexible instrument is configured or adapted to be inserted into the patient and to be located in the target area or volume. As the elongated flexible instrument comprises a sensor device, a cladding and an optical shape sensing device the elongated flexible instrument provides at least information relating to the position of the elongated flexible instrument and the amount of radiation received at that position. This allows for detection of movement of the patient, e.g. due to breathing or other reasons, and by detecting these movements, the radiation may be directed at the new location of the target area or target volume.

The optical shape sensing system is employed to track position of the target volume or target area. The present system also permits for rapid acquisition of three-dimensional (3D) volumetric sweeps of a catheter or a scope's elongated distal segment. This provides an electronic mapping or position determination of a 3D volumetric space, and provides volumetric point clouds which can facilitate registration and segmentation of intra/pre-procedurally acquired datasets.

Generally the system provides optical imaging based on optical frequency-domain interferometry using a rapidly-tuned wavelength-swept laser. Optical coherence tomography allows minimally-invasive cross-sectional imaging of biological samples and has been investigated for numerous applications in biology and medicine. In most optical coherence tomography systems, one-dimensional (depth) ranging is provided by low-coherence interferometry in which the optical path length difference between the interferometer reference and sample arms is scanned linearly in time.

One form of the present invention includes an optical shape sensing system employing the elongated flexible instrument, an optical fiber embedded within the elongated flexible instrument with the optical fiber including one or more cores, an optical interrogation console and a 3D shape reconstructor. In operation, the optical interrogation console generates reflection spectrum data indicative of a measurement of both amplitude and phase of a reflection for each core of the optical fiber as a function of wavelength and the 3D shape reconstructor reconstructs a 3D shape of the optical fiber. The 3D shape reconstructor executes a generation of local strain data for a plurality of positions along the optical fiber responsive to the reflection spectrum data, a generation of local curvature and torsion angle data as a function of each local strain along the fiber, and a reconstruction of the 3D shape of the optical fiber as a function of each local curvature and torsion angle along the optical fiber.

Advantageously the cladding is a scintillating cladding. The cladding is preferably located on one or more optical fibers in the flexible instrument. The cladding may be optimized for different energies of the incoming radiation, e.g. for diagnostic X-ray energies or for photon energies used in radiation therapy.

Advantageously the sensor device comprises multiple areas of cladding distributed along a length of the sensing device. By having multiple sites or areas of cladding distributed along a part of the sensing device a better resolution is achieved.

Advantageously the sensor device includes a configurable volume having a cladding. The configurable volume may then be used in such a fashion that a more extended 3D spatial sampling of dose/spectral characteristics may be obtained and reconstructed when combining sparse measurements with an appropriate biophysical/dose model to obtain a 3D volumetric map of dose/radiation spectrum characteristics during, or after, the procedure. Advantageously the configurable volume may be established using a deployable balloon, a filter device, a helix or a combination thereof. The specific embodiment may be selected based on the type of tissue that the device is to be inserted into.

Advantageously the optical shape sensing device may include an optical fiber having at least one of Fiber Bragg Gratings (FBGs) and/or a Rayleigh scatter interrogation setup for sensing strain in the fiber. The use of optical fiber or optical fibers allow for the device to be flexible. Other suitable materials or structures may be envisioned.

Advantageously the optical shape sensing device includes an area of higher sensitivity by including an area with a higher number of optical fibers having optical strain sensors. E.g. optical shape sensing device may have one area where one number of optical fibers having optical strain sensors are present, in another are another number of optical fibers having optical strain sensors is present, and thus an area having of higher sensitivity may be established. The higher sensitivity may help achieve a better resolution on the determination of the position of the device. It may be advantageous to have an area having one optical fiber having optical strain sensors defining an area having a first sensitivity, and another area having four optical fibers having optical strain sensors defining an area having a second sensitivity being higher than the first sensitivity.

Advantageously the optical shape sensing device may include one, or more, of a spiral shape, a ring shape, a straight or curved line and/or a loop shape. The different devises provide different effects e.g. better fitting to a specific organ and/or tumor, and the specific choice may depend on the intended clinical application.

In a second aspect the present invention provides a sensor device for detecting dose of radiation received at the sensor device. According to the teachings of the present invention the sensor device may comprise a flexible body having a cross-section being comparatively small relative to the length of the device, a cladding at the flexible body, the cladding converting incoming radiation into visible light, and an optical shape sensing device disposed within the flexible body and configured to determine a shape of the flexible instrument relative to a reference, the shape sensing device configured to collect information based on its configuration to map an intraluminal structure during a procedure.

The sensor device according to the second aspect may include any of the features mentioned in relation to the first aspect.

For instance the cladding may advantageously be a scintillating cladding. Further advantageously the sensor may further comprise a configurable volume having a cladding. Even further advantageously the configurable volume may be established using a deployable balloon, a basket, a filter device, a helix or a combination thereof. The configurable volume may be adapted to fit to or have a geometry corresponding to a specific organ or tumor shape.

In a third aspect the present invention provides a method of operating a radiation therapy system comprising a movable radiation source for directing and providing radiation to a designated target area or target volume, an elongated flexible instrument comprising a sensor device detecting dose of radiation received at the sensor device, the sensor device including a cladding converting incoming radiation into visible light, an optical shape sensing device disposed within the flexible instrument and configured to determine a shape of the flexible instrument relative to a reference, the shape sensing device configured to collect information based on its configuration to map an intraluminal structure during a procedure, a detector connected to the sensor device for detecting the visible light so as to determine the dose of radiation received at the sensor device, and a processor for operating the movable radiation source in relation to a predetermined target radiation dose and the determined dose of radiation. The method may comprise the steps of positioning the movable radiation source so as to direct and provide radiation to the designated target area or target volume, detecting the dose of radiation received at the sensor device, and operating the movable radiation source in response to the detected dose of radiation received.

The method may be computer implemented so as to control the operation of a system, e.g. according to the first aspect of the present invention. The sensor device is preferably a sensor device according to the second aspect of the present invention.

The method provides possibility to perform radiation therapy whilst taking into account movement in the patient, e.g. due to breathing as described above. Thereby a more efficient radiation therapy is achieved and the patient is subjected to less radiation as the supplied radiation is more efficient, this may result in less radiation therapy sessions, reduced beam width of the radiation source as the beam may be better focused during therapy and other beneficial effect of tracking movement in the target volume or area.

Advantageously the method may comprise the step of determining the position of the sensor device using optical Rayleigh-scattering.

Advantageously the method may comprise the step of determining orientation of the elongated flexible member using the optical shape sensing device.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which FIG. 1 schematically illustrates a configuration of Optical frequency domain reflectometry using a tuneable light source and a fiber-optic interferometer, FIG. 2 schematically illustrates an optical shape sensing system, FIG. 3 schematically illustrates a catheter with a number of different scintillating claddings along the catheter for on-line radiation measurements, FIG. 4 schematically illustrates a catheter with a radiation measuring cladding at the tip of the catheter for on-line guidance of a radiation therapy system, FIG. 5 schematically illustrates a scintillating fiber dosimeter array/flexible photon detector mesh with shape sensing, FIG. 6 schematically illustrates steps of a method according to the present invention, FIG. 7 schematically illustrates a sensor device having a configurable volume in a relaxed state, and FIG. 8 schematically illustrates a sensor device having a configurable volume in an engaged state.

DESCRIPTION OF EMBODIMENTS

The present disclosure describes systems and methods for a radiation dosage sensing device in combination with an optical shape sensing fiber tracking system. The device may additionally designed to be imagable using a range of different ways including, but not limited to kV or MV X-ray imaging in the radiotherapy setup, or Ultrasound, further pre-interventional imaging including but not limited to CT, MR, X-ray, Ultrasound imaging could be performed. The present embodiments make use of shape reconstruction capabilities of optical sensing shape-based volumetric definition for live processing of 3D imaging data for optimising radiation treatment.

Figure 1:
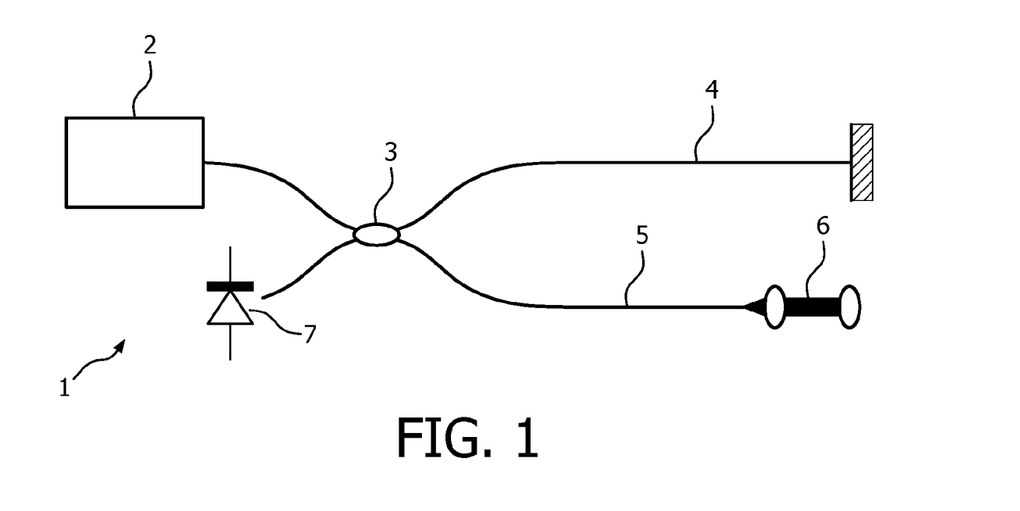

FIG. 1 schematically illustrates the principles in a configuration of a system 1 for optical frequency domain reflectometry using a tuneable light source 2 and a fiber-optic interferometer. The output of the light source 2 travels through a splitter 3 which directs a part of the signal into a reference arm 4 and the remaining part of the signal into a sample arm 5 which illuminates and receives the light reflected at the area 6.

The area 6 corresponds to the cladding areas 54 described below.

The interference between the signal returned from the reference arm and the signal returned from the sample-arm is detected with a square-law photo detector 7 while the wavelength of the monochromatic source is swept and the path lengths of the reference and sample arm are held constant. The axial reflectivity profile (A-line) is obtained by discrete Fourier transform (DFT) of the sampled detector signals. The principles are similar to those used in the systems described below.

Figure 2:
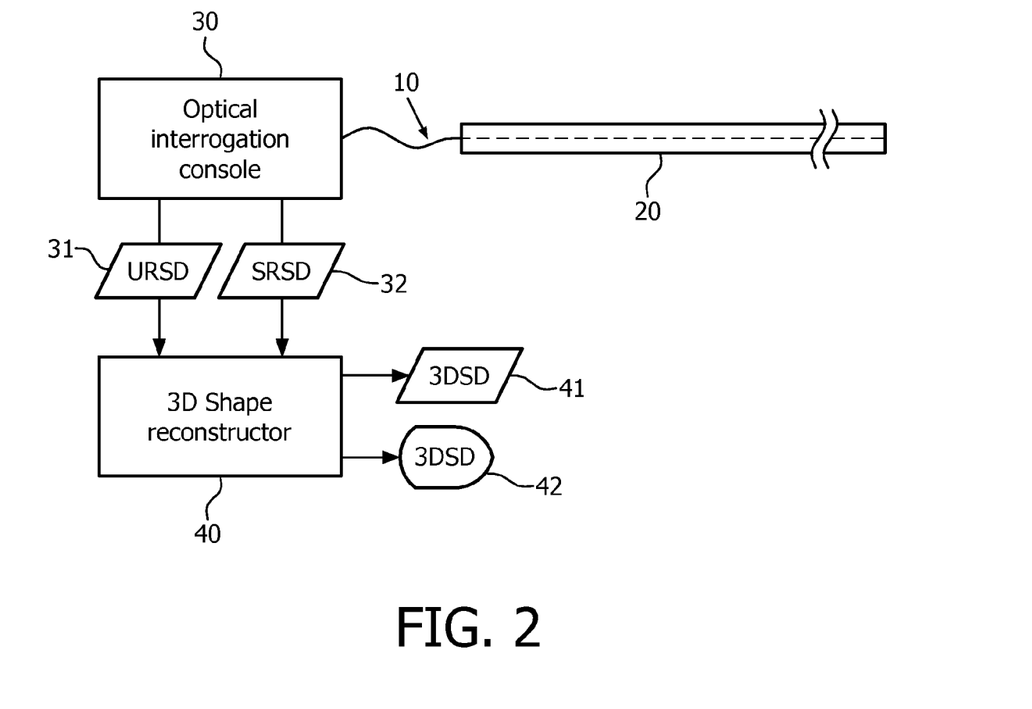

FIG. 2 schematically illustrates an optical shape sensing system which employs an optical core 10 embedded within an elongated device 20. In practice, optical fiber 10 may be any type of optical fiber suitable for optically tracking elongated device 20. Examples of optical fiber 10 include, but are not limited to, a flexible optically transparent glass or plastic fiber incorporating an array of fiber Bragg gratings integrated along a length of the fiber as known in the art, and a flexible optically transparent glass or plastic fiber having naturally variations in its optic refractive index occurring along a length of the fiber as known in the art (e.g., a Rayleigh scattering based optical fiber). Optical fiber 10 may be a single core fiber or preferably, a multi-core fiber.

In practice, elongated device 20 may be any type of device suitable for embedding an optical fiber therein for purposes of optically tracking the elongated device. Examples of elongated device 20 include, but are not limited to, an endoscope of any type, a catheter and a guide wire.

Still referring to FIG. 2, the system further employs an optical interrogation console 30 and a 3D shape reconstructor 40.

In practice, optical interrogation console 30 may be any device or system structurally configured for transmitting light to optical fiber 10 and receiving reflected light from optical fiber 10. In one embodiment, optical interrogation console 30 employs an optical Fourier domain reflectometer and other appropriate electronics/devices as known in the art.

For purposes of the present invention, 3D shape reconstructor 40 is broadly defined herein as any device or system structurally configured for translating measured reflection spectra data of optical fiber 10 into a 3D shape of optical fiber 10 and elongated device 20. The 3D shape reconstructor 40 includes a processor for performing suitable calculations.

Figure 3:
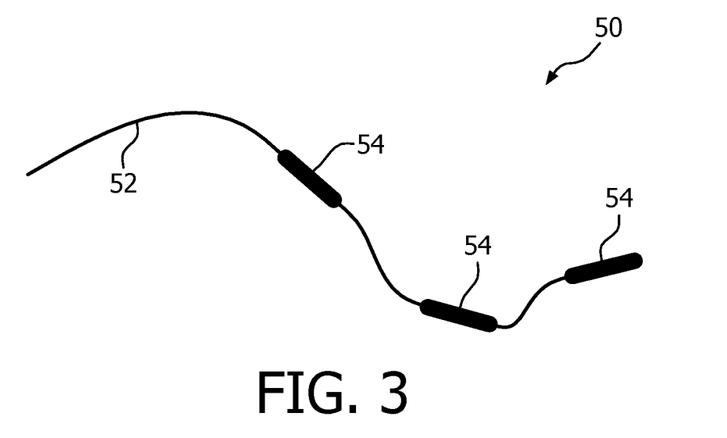

An embodiment of the invention is illustrated in FIG. 3 where a sensor device 50 for detecting dose of radiation received at the sensor device is schematically illustrated. The sensor device 50 comprises a flexible body 52 having a cross-section being comparatively small relative to the length of the device 50. The sensor device 50 includes cladding 54 at the flexible body 52, in this embodiment three cladding areas are illustrated, in other embodiments more or less areas may be provided. The cladding 54 converts incoming radiation into visible light. The sensor device 50 includes an optical shape sensing device disposed within the flexible body and configured to determine a shape of the flexible instrument relative to a reference, the shape sensing device configured to collect information based on its configuration to map an intraluminal structure during a procedure. The sensor 50 may be used in connection with an apparatus as described in relation to FIGS. 1 and/or 2, e.g. the optical interrogation console 30.

Figure 4:
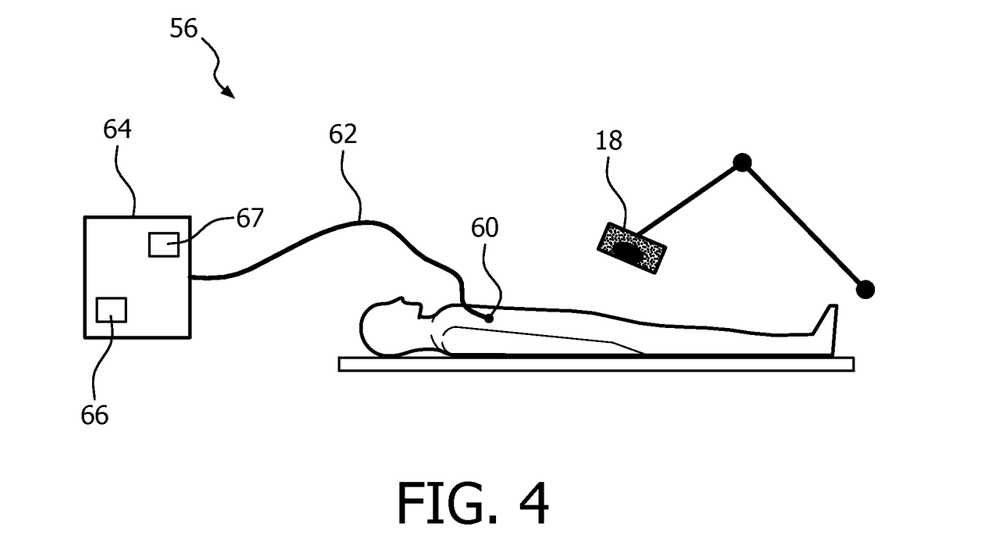

FIG. 4 schematically illustrates a radiation therapy system 56 comprising a movable radiation source 18 for directing and providing radiation to a designated target area or target volume 60. An elongated flexible instrument 62 is provided. The elongated flexible instrument 62 is of the type described in relation to FIG. 3 and comprise any features mentioned in relation to the discussed presented there. The sensor 62 is connected to an optical system 64 similar to the optical interrogation console 30 described above. The system 64 comprises a detector 67 that is connected to the sensor device for detecting the visible light. In this way, the detector is able to determine the dose of radiation received at the sensor device. The system 64 further comprises a processor 66 for performing the mentioned method steps described later. The processor 66 is configured or adapted to operating the movable radiation source 18 in relation to the predetermined target radiation dose and the determined dose of radiation. The processor may be configured or adapted via a software product implementing the steps of the method according to the present invention. The processor may in some embodiments be constituted by several processors, where one processor is configured or adapted to operate the radiation therapy part and another processor is adapted to perform measurements. Further the processor 66 is used for directing the radiation to the designated target area or volume 60 as the patient moves, e.g. breathes. This is done in response to the position determination of the fiber as described elsewhere.

Generally optical shape sensing utilizes special optical fibers which are integrated in a catheter or device and connected to an analysis unit outside the body of the patient. The position and the shape of the fiber is measured in real time using modeling and analysis of the optical Rayleigh scattering with respect to the analysis unit attached to one end of the device. In order to combine this optical shape sensing with a radiation measurement unit, one or more additional optical fibers are added which have a scintillating cladding at one or a number of distances along the device, which is illustrated e.g. in FIG. 3.

The scintillating claddings may be optimized for different energies of the incoming radiation, e.g. for diagnostic X-ray energies or for photon energies used in radiation therapy. They convert the incoming photons into visible light and therefore, they allow quantification of the radiation reaching different areas of the catheter or its tip.

In the scenario mentioned above, the device, i.e. the elongated flexible instrument, may advantageously be used as follows:

In radiation therapy the device is located close to or inserted into the tumor. The device is used for measuring or determining the 3D position continuously and thereby guides the radiation beam of the radiation therapy unit even in the case of breathing motion, cardiac motion, peristaltic motion, or other patient induced movements. In addition, the beam is controlled by the device by quantifying the applied dose to the tumor by real time measurement via the integrated radiation sensor. In the case that the sensor measures no or low radiation, the radiation beam may be modulated in intensity or shut down since it is not hitting the tumor anymore in close proximity to the sensor. A recalibration/retargeting of the system may be triggered by this dose sensing feedback control loop. If the dose measured at the tip of the device reaches the session limit the radiation is stopped.

The joint measurement of shape/localization with radiation dosimetry measurements can be exploited within a novel shaped instrument wherein the dose sensing shape distribution extends over a configurable volume/spatial extent (e.g. via a deployable balloon, filter device, or helix). In such a fashion, a more extended 3D spatial sampling of dose/spectral characteristics can be obtained and reconstructed when combining sparse measurements with an appropriate biophysical/dose model to obtain a 3D volumetric map of dose/radiation spectrum characteristics in the procedure. These measurements can also be combined with other biophysical parameter measurements e.g. flow, temperature, etc., to obtain functional as well as morphologically changes induced by radiation therapy.

The radiation probe sensor may be swept in time with continuous recording of sensor measurements to obtain a dynamically evolving volumetric map of radiation therapy effects.

Measurements of radiation dose at differential segments of the elongated flexible dose sensor can be used in a computation model of radiation therapy delivery to automatically trigger modulation of the therapy beam properties or other imaging/therapy system functionality.

Advantages and applications:

Additional scenarios may arise in a combination with nuclear medicine guided interventions.

The claddings which are connected to the catheter/device may only be partial claddings or may be radiation shielded, in order to derive additional directional information on the radiation which is reaching the catheter/device.

Figure 5:
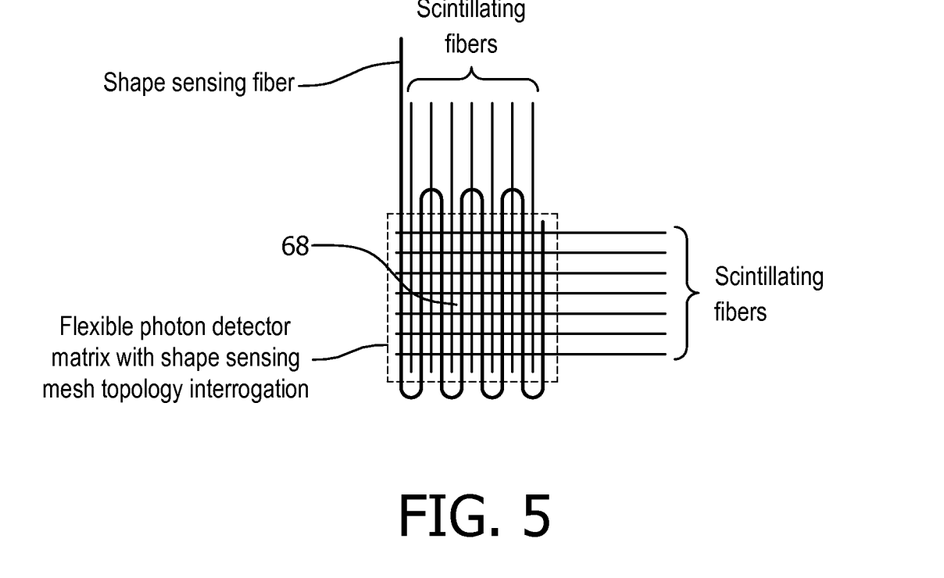

In an embodiment, as schematically illustrated in FIG. 5, a scintillating fiber dosimeter array 68 can be built having an interweaved shape sensing fiber or scintillating shape sensing fiber. This setup allows for a belt-type device or similar body/organ contour conforming matrix/flexible sensor array which can track organ deformation as well as locally applied dose for external beam radiation therapy.

Figure 6:
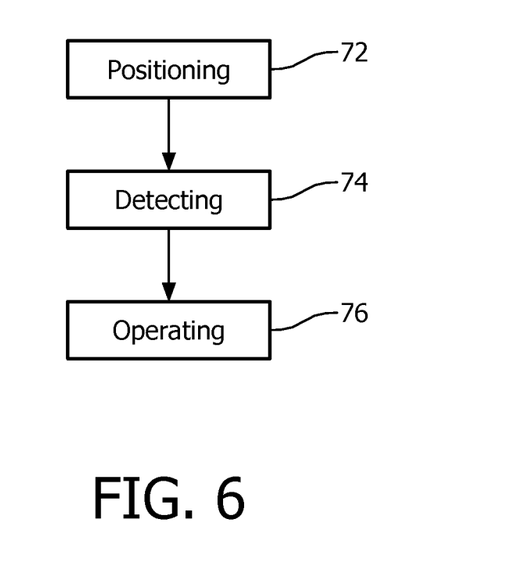

FIG. 6 schematically illustrates steps of an embodiment of a method 70 of operating a radiation therapy system comprising a movable radiation source for directing and providing radiation to a designated target area or target volume, an elongated flexible instrument comprising a sensor device detecting dose of radiation received at the sensor device, the sensor device including a cladding converting incoming radiation into visible light, an optical shape sensing device disposed within the flexible instrument and configured to determine a shape of the flexible instrument relative to a reference, the shape sensing device configured to collect information based on its configuration to map an intraluminal structure during a procedure, a detector connected to the sensor device for detecting the visible light so as to determine the dose of radiation received at the sensor device, and a processor for operating the movable radiation source in relation to a predetermined target radiation dose and the determined dose of radiation, the method comprising the steps positioning 72 the movable radiation source so as to direct and provide radiation to the designated target area or target volume, detecting 74 the dose of radiation received at the sensor device, and operating 76 the movable radiation source in response to the detected dose of radiation received. The method is preferably used for controlling and operating a system as described in FIG. 4.

The method is preferably computer implemented and may include steps of operating any features of the system described in relation to FIG. 1 or 2 and/or using the device described in relation to FIG. 3 or 5.

Figure 7:
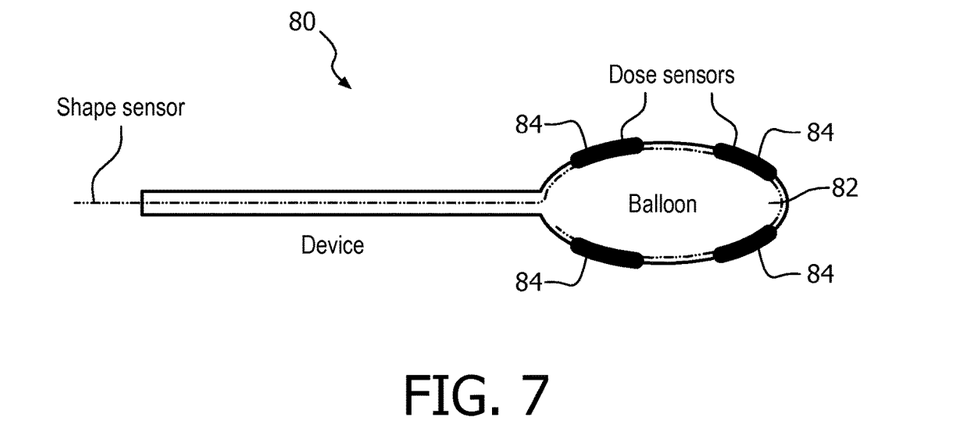

FIG. 7 schematically illustrates a sensor device 80 having a configurable volume, here in the form of a balloon 82, in a relaxed state. The balloon 82 may be packed into a catheter when being inserted through the body of a patient and then be deployed to the state illustrated in FIG. 7. In the balloon 82, or on the surface thereof, is mounted a number of dose sensors 84.

Figure 8:
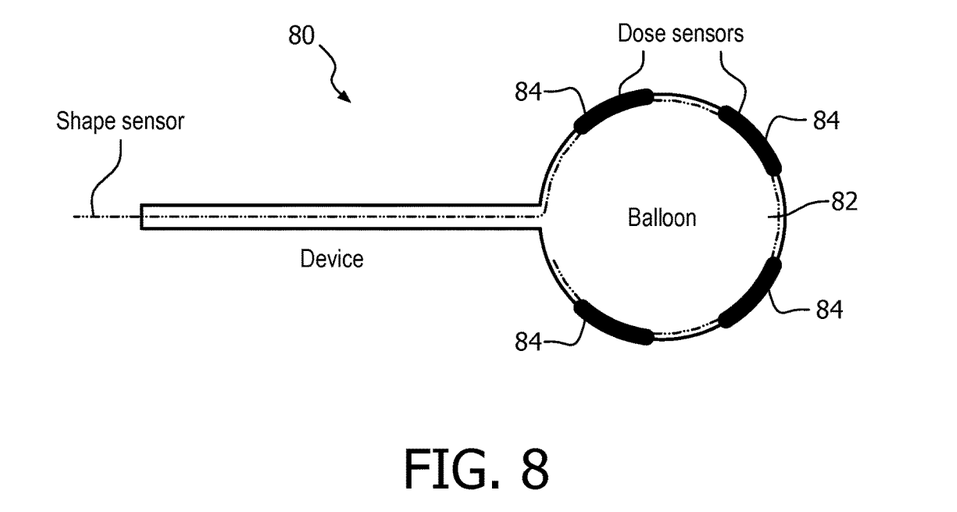

FIG. 8 schematically illustrates the sensor device 80 having a configurable volume, i.e. the balloon 82, in an engage state. The configurable volume may be engaged by use of an inert gas or the like.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A sensor device for detecting dose of radiation received at the sensor device, the sensor device comprising:
   a flexible body having a cross-section being comparatively small relative to the length of the device,
   a cladding at the flexible body, the cladding converting incoming radiation into visible light, and
   an optical shape sensing device disposed within the flexible body and configured to determine a shape of the sensor device relative to a reference, the shape sensing device configured to collect information based on its configuration to map an intraluminal structure during a procedure,
   wherein the cladding is a scintillating cladding.

2. The sensor device according to claim 1, further comprising a configurable volume having the cladding or a second cladding.

3. The sensor device according to claim 2, further comprising a deployable balloon, a basket device, a filter device, a helix or a combination thereof extendable over the configurable volume.

4. A radiation therapy system comprising an optical shape sensing device according to claim 1, the radiation therapy system further comprising:
   a movable radiation source for directing and providing radiation to a designated target area or target volume,
   a detector connected to the sensor device for detecting the visible light so as to determine the dose of radiation received at the sensor device, and
   a processor for operating the movable radiation source in relation to a predetermined target radiation dose and the determined dose of radiation.

5. The radiation therapy system according to claim 4, wherein the cladding at the flexible body of the sensor device comprises multiple areas of the cladding distributed along a length of the sensing device.

6. The radiation therapy system according to claim 4, wherein the sensor device includes a configurable volume having the cladding or a second cladding.

7. The radiation therapy system according to claim 6, further comprising a deployable balloon, a basket device, a filter device, a helix or a combination thereof extendable over the configurable volume.

8. The radiation therapy system according to claim 4, wherein the optical shape sensing device includes an optical fiber having at least one of Fiber Bragg Gratings (FBGs) and/or a Rayleigh scatter interrogation setup for sensing strain in the fiber.

9. The radiation therapy system according to claim 4, wherein the optical shape sensing device includes an area of higher sensitivity relative to a sensitivity of an area with a lower number of optical fibers having optical strain sensors, the area of higher sensitivity including an area with a number of optical fibers having optical strain sensors that is higher than in the area with the lower number of optical fibers having optical strain sensors.

10. The radiation therapy system according to claim 4, wherein the optical shape sensing device comprises an optical fiber having one of a spiral shape, a ring shape a straight or curved line and/or a loop shape.

11. A method of operating a radiation therapy system comprising a movable radiation source for directing and providing radiation to a designated target area or target volume, an elongated flexible instrument comprising a sensor device detecting dose of radiation received at the sensor device, the sensor device including a scintillating cladding converting incoming radiation into visible light, an optical shape sensing device disposed within the flexible instrument and configured to determine a shape of the flexible instrument relative to a reference, the shape sensing device configured to collect information based on its configuration to map an intraluminal structure during a procedure, a detector connected to the sensor device for detecting the visible light so as to determine the dose of radiation received at the sensor device, and a processor for operating the movable radiation source in relation to a predetermined target radiation dose and the determined dose of radiation, the method comprising the steps:
   positioning the movable radiation source so as to direct and provide radiation to the designated target area or target volume,
   detecting the dose of radiation received at the sensor device, and
   operating the movable radiation source in response to the detected dose of radiation received.

12. The method according to claim 11, wherein the position of the sensor device is determined using optical Rayleigh-scattering.

13. The method according to claim 11, further comprising:
   determining orientation of the elongated flexible member using the optical shape sensing device.

* * * * *